United States Patent [19]
Di Napoli

[11] Patent Number: 5,864,048
[45] Date of Patent: Jan. 26, 1999

[54] RHEIN DERIVATIVES AND NEW PROCESSES FOR PRODUCING RHEIN DERIVATIVES

[75] Inventor: Guido Di Napoli, Collonge Bellerive, Sweden

[73] Assignee: Laboratoire Medidom S.A., Switzerland

[21] Appl. No.: 903,660

[22] Filed: Jul. 31, 1997

[30] Foreign Application Priority Data

Jul. 31, 1996 [IT] Italy .................................. MI96A1655

[51] Int. Cl.⁶ ...................................... C07L 50/26
[52] U.S. Cl. .......................................... 552/307; 552/290
[58] Field of Search ................................ 52/307; 552/290

[56] References Cited

U.S. PATENT DOCUMENTS 3,089,879   5/1963   Serres et al. .

FOREIGN PATENT DOCUMENTS

| 0636602 | 2/1995 | European Pat. Off. . |
| 80407 | 10/1894 | Germany . |
| 193104C | 12/1907 | Germany . |
| 1578452 | 5/1980 | United Kingdom . |

OTHER PUBLICATIONS

Abstract, JP 49045050A (1974).
European Search Report, The Hague, Nov. 11, 1997, Examiner Kinzinger, J.
Journal of the Chem. Soc., Section C: Organis Chemistry, pp. 307–311 (1970).
Abstract, DE 2315728, Planta Bed., vol. 19, pp. 363–365 (1970–1971).
Abstract, DE 2481232, Biochem. J., vol. 92, pp. 369–377 (1964).
Abstract, DE 2684047, Biochem., J., vol. 92, pp. 369–377 (1964).
Abstract, DE 2684626, 3467052, 3452932, 3501790, Helvetica Chimica Acta, vol. 8, pp. 128–137 (1925).
Abstract, DE 3452914, Proc.–Indian Acad. Sci. Sect. A, vol. 33, pp. 142–145 (1951).
Abstract, DE 5014406, Journal of Heterocyclic Chemistry, vol. 26, pp. 1404–1413 (1989).
Abstract, DE 2807300, Bulletin de La Societe Chimique De France, pager 1622 (1961).
Abstract, DE 4256071, Liebigs Annalen Der Chemie., No. 10, pp. 1047–1049 (1990).
Abstract, DE 4459267, Tetrahedron Letters, vol. 30, No. 7, pp. 869–872 (1989).
Journal of the Chemical Society, No. 2, pp. 445–447 (1987).
Tetrahedron., vol. 42, No. 12, pp. 3303–3309 (1986).

*Primary Examiner*—Paul J. Killos
*Attorney, Agent, or Firm*—Hedman, Gibson & Costigan, P.C.

[57] ABSTRACT

The present description relates to new anthraquinone-derivatives endowed with inhibitory activity of the serine proteinase enzymes, useful for the treatment of rheumatoid arthritis, acute respiratory syndrome of adult, and pulmonary emphysema, and to new processes for the preparation of rhein derivatives.

17 Claims, No Drawings

RHEIN DERIVATIVES AND NEW PROCESSES FOR PRODUCING RHEIN DERIVATIVES

FIELD OF THE INVENTION

The present invention relates to new rhein derivatives useful in the treatment of diseases associated with abnormal degeneration of the connective tissue, and to new processes for producing rhein derivatives from synthetic raw materials.

1. Prior Art

Rhein and several analogues thereof, out of which diacerhein is particularly important from a commercial point of view, are known for use in the treatment of degenerative diseases of the joints, such as for example osteoarthritis, osteoporosis and rheumatoid arthritis (GB 1,578,452).

The only process for diacerhein synthesis utilized at present on a commercial scale is based on the use of aloin as raw material (European patent application No. 636,602 A1, by the Applicant). DE 80,407 and U.S. Pat. No. 3,089,879-A describe ring closure of 2,4'-benzophenone dicarboxylic acid to 2-carboxy-antraquinone by treatment with sulphuric acid. Japanese Application JP 49/45050 reports acid catalyzed cyclization of 2-(2'aminobenzoyl)-benzoic acid to 1-aminoantraquinone. In principle, two isomeric substituted 1-aminoantraquinones can be formed by cyclization of 2-(2'-aminobenzyl)-benzoic acid. So, these documents do in no way suggest that ring closure to 1-aminoantraquinone of diarylketones of formula (II) according to step a) of the present process as below illustrated allows the isomeric 1-aminoantraquinone of formula (III) to be obtained in high yield and in pure form.

2. Technical Problem

Aloin is obtained from natural sources via laborious extraction and purification procedures consuming large amounts of vegetable raw materials. The periodical cost fluctuations of the raw material of vegetable origin is a serious disadvantage, the prices of pharmaceuticals being strictly governed by the regulations in force.

Furthermore, with the use of vegetable raw materials it is not always possible to obtain rhein derivatives functionalized at will on the anthraquinone nucleus, the successive substitution reactions on said nucleus often occurring in low yields and/or not allowing substitutions at the desired positions.

Therefore, the need for a commercial-scale process for the production of diacerhein derivatives of good purity and in satisfactory yields, which would not cause the inconveniences inherent in the known processes, is deeply felt.

SUMMARY

The present invention is directed to new rhein derivatives of formula (I),

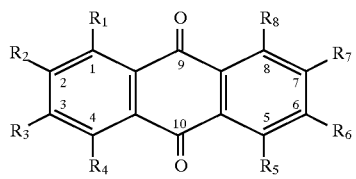

where $R_2=R_4=R_5=H$ and where:
$R_1$ is —ORa or —OCORa, and $R_8$ is ORb or —OCORb or halogen, where Ra and Rb, which may be the same or different one from another, each represents H, alkyl or aromatic group, $R_6$ is —COORc, —CONRdRe, —CH$_2$OCORf, —CH$_2$ORg, where Rc, Rd, Re and Rf, which may be the same or different one from another, each represents H, alkyl or aromatic group, and Rg is an alkyl or aromatic group, $R_3$ is H or an —ORh or —OCORh, where Rh is H, alkyl or aromatic group;

$R_7$ is H, an alkyl, alkenyl, alkynyl, or arylalkyl group, and the pharmaceutically acceptable salts thereof, provided that at least $R_3$ or $R_7$ is different from H, and being further provided that the compounds of formula (I), where $R_2=R_4=R_5=H$, selected among those where:

$R_6$ is —COOH or —CH$_2$OH, and $R_1=R_8=R_3$=—OH;

$R_6$ is —COOCH$_2$CH$_3$ or —CH$_2$OCOCH$_3$; $R_1=R_3$=—OCH$_3$ and $R_8$=OH; and $R_6$ is —COOH, —COOCH$_2$CH$_3$ or —CH$_2$OCOCH$_3$, $R_3$=—CH$_3$ and $R_1=R_8$=—OH, are excluded.

The new rhein derivatives according to the present invention show substitutions on the aromatic rings of the anthraquinone structure at position 7 and/or 3. It was, therefore, impossible to obtain them by conventional syntheses using raw materials of natural origin, through substitutions on the aromatic rings of the preformed anthraquinone structure.

It has been surprisingly found that the aforesaid new rhein derivatives significantly inhibit the serine proteinase enzymes, in particular the human leukocytal elastase (HLE) and cathepsin G (Cat G), said two enzymes being capable of restoring the proteinase-antiproteinase balance, which is extremely subjected to inactivation by oxidative stress promoters.

Serine proteinase HLE and Cat G are involved in elastin degradation. The hypothesis has been proposed that they are involved in the connective tissue abnormal degeneration associated with various diseases, such as rheumatoid arthritis, acute respiratory syndrome of adult, and pulmonary emphysema.

The aforesaid activity of the new rhein derivatives is especially unexpected since diacerhein, which from a commercial point of view, is the most interesting of all rhein derivatives, is substantially free from serin protease enzymes inhibitory activity.

Therefore, the present invention also includes (i) the use of new rhein derivatives of formula (I) of the invention in the treatment of diseases associated with an abnormal degeneration of the connective tissue, e.g. inflammatory states of the joints and of the connective tissue, such as for example rheumatoid arthritis, osteoarthritis, osteoporosis, or of other diseases, such as acute respiratory syndrome of adult (e.g: asthma) and pulmonary emphysema, and (ii) the pharmaceutical compositions containing said new rhein derivatives.

The Applicant has also surprisingly found a new process for producing rhein derivatives functionalized at will on the anthraquinone nucleus, meant in particular for the preparation of rhein derivatives of formula (I)

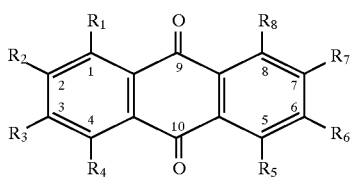

in which $R_1$ is —ORa or —O—CO—Ra and $R_8$ is , —ORb, —O—CO—Rb or halogen, where Ra and Rb, which are the same or different one from another, each represents H, alkyl or aromatic group;

$R_6$ is —COOH, —COORc, —COSRf, —CONRdRe, —CH$_2$—O—CORf, —CH$_2$ORg, where Rc is an alkyl or aromatic group, and Rd, Re, Rf, Rg, which are the same of different one from another, each represents H, or an alkyl or aromatic group;

$R_2$, $R_3$, $R_4$, $R_5$, and $R_7$, which are the same or different one from another, each represents H or a group selected out of an alkyl, alkenyl, alkynyl, hydroxy, alcoxy, acyloxy, arylalkyl, aromatic and cyano group, provided that at least one of substituents $R_2$, $R_3$, $R_4$, $R_5$, and $R_7$ is different from H, comprising the steps of:

a) treating a diarylketone of formula (II)

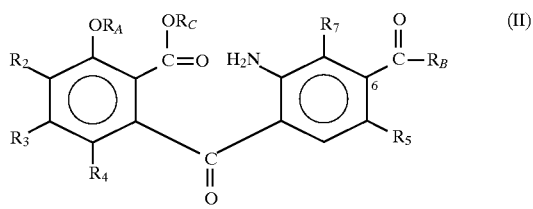

in which $R_A$ is H or a protective group of the —OH function, and typically $R_A$ is Ra or —CORa, where Ra represents H or an alkyl or aromatic group, $R_B$ is selected out of —ORc, —NRdRe, —SRf, where Rc, Rd, Re, and Rf, which are the same or different one from another, each represents H, alkyl or aromatic group, $R_C$ is H or a short-chain alkyl (such as for example $C_1$–$C_4$ alkyl), and $R_2$, $R_3$, $R_4$, $R_5$, and $R_7$ are as defined above for the derivatives of formula (I), with a strong concentrated acid (e.g. a superacid) to give the 1-aminoanthraquinone derivative of formula (III)

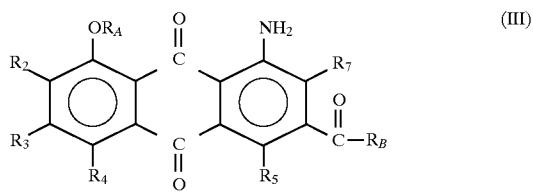

in which $R_A$, $R_B$, $R_2$, $R_3$, $R_4$, $R_5$, and $R_7$ are as defined in the present step;

b) converting the —NH$_2$ group into —OH, via the following steps:

b') treating the derivative of formula (III) obtained in step a) with a diazotising agent;

b'') warm treating the product resulting from step b') with a strong acid in an aqueous medium to give the compound of formula (IV)

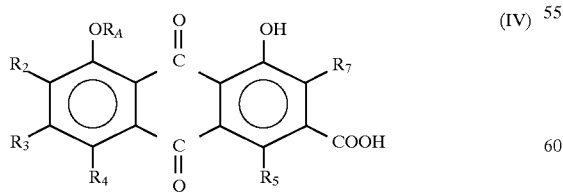

in which $R_A$, $R_2$, $R_3$, $R_4$, $R_5$, and $R_7$ are as defined above or, b''') to obtain compounds of formula (I) wherein $R_8$ is halogen, subjecting the products coming from step b') to replacement of the diazonium group by halogen according to known techniques, e.g. by treatment with a cuprous halide such as CuCl or CuBr.

The present process may optionally include the additional steps illustrated below: step c): when, in compounds (II), (III) and (IV), $R_A$ is a protective group and the derivatives of formula (I), in which $R_1$ is —OH, are to be obtained, the $R_A$ group is removed on the compound of formula (II) or (III) or (IV), in which $R_A$ is a protective group as defined above. In that case, once steps a), b'), b''), and c) have been performed a rhein derivative of formula (V)

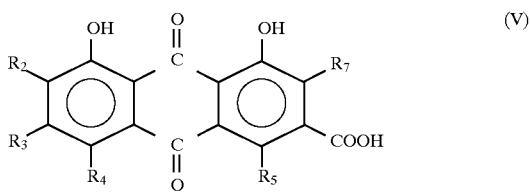

in which $R_2$, $R_3$, $R_4$, $R_5$ and $R_7$ are as defined in step b'') above [which corresponds to the derivative of formula (I), in which $R_1$=$R_8$=OH] is obtained;

step d): to obtain the derivative of formula (I), in which $R_1$, $R_8$ or both are —OCORa, where Ra is H, alkyl or aromatic group, the corresponding rhein derivative of formula (I) or (II) or (III) or (IV), in which $R_1$, $R_8$ or both are —OH, or compounds (II)A, in which $R_A$ is H, or the corresponding derivatives of formula (V) are treated with an acylating agent (e.g. acid halide or anhydride of a carboxylic acid RaCOOH or RbCOOH);

step d'): to obtain the derivatives of formula (I), in which $R_1$, $R_8$ or both are —ORa or —ORb, where Ra and Rb represent an alkyl or aromatic group, the corresponding compounds of formula (I) or (II) or (III) or (IV), in which $R_1$, $R_8$ or both are —OH, or compounds (II)A, in which $R_A$ is H, or the corresponding derivatives of formula (V) are subjected to etherification (e.g. by treatment with a halide RaHal or RbHal, where Ra and Rb represent an alkyl or aromatic group, in the presence of a base capable of removing the phenol proton, e.g. NaH).

In any case, acylation or etherification may be carried out by other conventional techniques.

The derivatives of formula (I), in which $R_6$ is —COOH, may be converted, by known methods, into the corresponding derivatives of formula (I), in which $R_6$ represents —COORc, —COSRf, —CONRdRe, —CH$_2$—O—CORf, —CH$_2$ORg, where Rc, Rd, Re, Rf, Rg, which may be the same or different one from another, each represents H or an alkyl or aromatic group, and Rc is different from H, for instance by converting the —COOH group into the —COORc group, e.g. by treating derivative (I), in which $R_6$ is —COOH, with an alcohol RcOH, typically in the presence of an acid catalyst, such as H$_2$SO$_4$;

converting the —COOH or —COORc group into the —COORc, —COSRf, —CONRdRe, by treating them with the corresponding alcohol RcOH (Rc different from H), or with a compound RfSH, RdReNH, respectively, typically in the presence of a catalyst (e.g. acid or basic);

converting the —COOH group into the —CH$_2$OH group by reduction with LiAlH$_4$ or LiBH$_4$, optionally followed by treatment with an acylating agent (RfCOOH acid halide or anhydride) or with an etherifying agent e.g. a halide RgHal (Rg different from H), where Rf and Rg are as defined above and Hal is a halogen, thus converting the $CH_2$—OH group into —$CH_2$—O—CORg or the —$CH_2$ORg groups, respectively.

The aforesaid conversions may be carried out not only on the derivatives of formula (I) but also on all the aforementioned synthesis intermediates of the present process [(II), (III), (IV), (V)] or on intermediates (VI), (II)A or (XI) that will be illustrated hereinafter.

The present invention also includes the diarylketones of formula (II), the 1-aminoanthraquinones derivatives of formula (III), the compounds of formula (IV), and the diazoderivatives of formula (VI) that will be described hereinafter.

The present invention also provides a process for the preparation of a diarylketone of formula (II)A

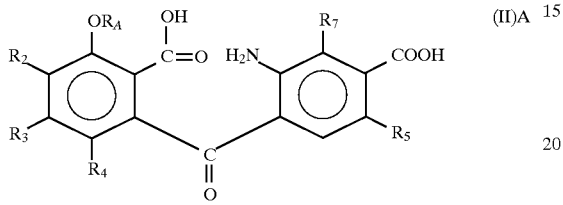

in which $R_A$ represents the protective group of the —OH function, and $R_2$, $R_3$, $R_4$, $R_5$ and $R_7$ are as defined above for the compounds of formula (I) comprising the following steps:

1) the phthalic acid derivative of formula (VII)

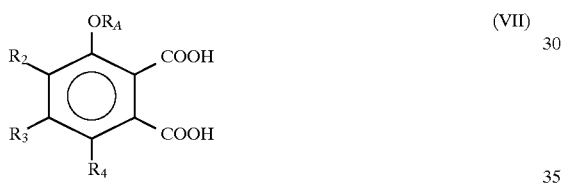

in which $R_A$ is a protective group of the —OH function, and $R_2$, $R_3$ and $R_4$ are as defined for the compound of formula (I), is treated with an $R_C$OH compound, where $R_C$ is an alkyl group, in the presence of a Cu(I) salt, in an acid medium, to give the monoester of formula (VIII)

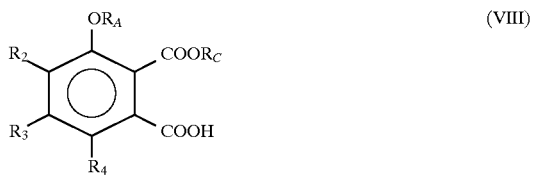

in which $R_A$, $R_C$, $R_2$, $R_3$, and $R_4$ are as defined above for this step;

2) the derivative of formula (VIII) obtained in the preceding step is treated with a halogenating agent of the carboxylic function to give the acyl halide of formula (IX)

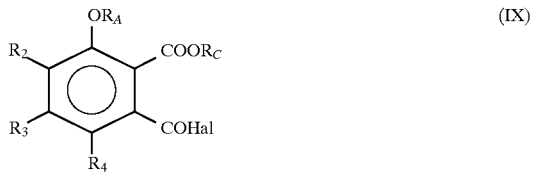

in which $R_A$, $R_C$, $R_2$, $R_3$, and $R_4$ are as defined in the preceding step, and Hal is a halogen;

3) the resulting derivative of formula (IX) is treated with a derivative of formula (X)

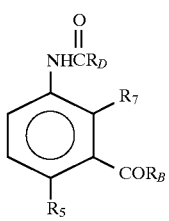

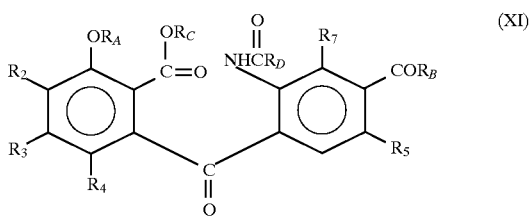

in which $R_B$ is selected from the group consisting of —ORc, —NRdRe, —SRf, where Rc and Rf are alkyl or aromatic groups, and Rd and Re, which may be the same or different one from another, each represents H, an alkyl or aromatic group, $R_D$ is an alkyl or aromatic group, and $R_5$ and $R_7$ are as defined for the compound of formula (I) to be prepared in the presence of a Friedel-Crafts catalyst, to give the diarylketone of formula (XI)

in which $R_B$, $R_C$, $R_D$, $R_2$, $R_3$, $R_4$, $R_5$, and $R_7$ are as defined in the preceding step, $R_A$ is as defined in step 1);

4) the protected diarylketone of formula (XI) is treated with a strong base, in an aqueous medium, and acidified to give the diarylketone of formula (II)A, in which $R_A$, $R_2$, $R_3$, $R_4$, $R_5$, and $R_7$ are as defined in the preceding step.

The derivative of formula (II)A may be converted, by known techniques, into the corresponding derivatives of formula (II), in which $R_B$ is —ORc, —NRdRe, —SRf, where Rd, Re, and Rf, which may be the same or different one from another, each represents H or an alkyl or aromatic group, and Rc is an alkyl or aromatic group, e.g. by treatment with an alcohol, an amino compound or a thiol (for example, with RcOH, $NH_3$, RdReNH or RfSH), and/or into the corresponding compounds of formula (II), in which $R_C$ is a short-chain alkyl, by treatment with the corresponding alcohol Rc OH.

The present invention also includes the diphenylketones of formulas (XI) and (II)A as defined above, and the itermediates of formulas (VII), (VIII) and (IX) as defined above, in which at least $R_2$, $R_3$ or $R_4$ is different from H, and the intermediates of formula (X) as defined above, in which at least $R_5$ or $R_7$ is different from H.

The process of the invention allows pure rhein derivatives of formula (I) to be obtained, in high yields, from synthetic reagents without using raw materials of extractive origin.

The Applicant has also found a further new process for the preparation of rhein derivatives of formula (XV)

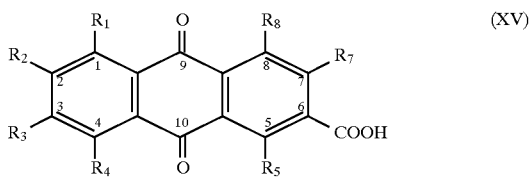

wherein $R_1$ is —ORa or —OCORa, and $R_8$ is —ORb or —OCORb, wherein Ra and Rb, equal or different one from another one from another, are selected among H, alkyl group and aromatic group; $R_2$, $R_3$, $R_4$, $R_5$, and $R_7$, equal or different one from another, are selected among H, alkyl, alkenyl, alkinyl, hydroxy, alkoxy, acyloxy, arylalkyl, aromatic and cyano group, provided that at least one of $R_5$ and $R_7$ is H, comprising the following steps:

e) subjecting to mono-nitration an anthraquinone derivative of formula (XVI)

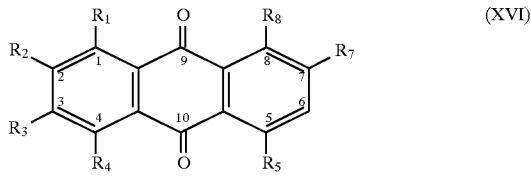

wherein $R_1$, $R_8$, $R_2$, $R_3$, $R_4$, $R_5$ and $R_7$, are as above defined for compound of formula (XV), by treating the compound of formula (XVI) with an essentially stoichiometric amount of nitric acid, thus affording the corresponding mono-nitro derivative selected from the group consisting of compound of formula (XVII)A, compound of formula (XVII)B, and mixtures thereof

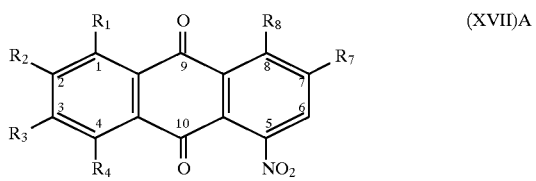

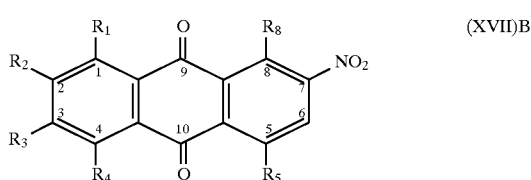

wherein $R_1$, $R_8$, $R_2$, $R_3$, $R_4$, $R_5$ and $R_7$, are as above defined for compound of formula (XVI);

f) treating the mono-nitro derivative obtained from the preceding step with cyanide ions, to give the carboxy antraquinone derivative of formula (XV) as above defined.

Conversion of nitro group into carboxy group by means of cyanide treatment according to step f) occurs under the conditions of the von Richter rearrangement, which, to the Applicant's knowledge, has never been applied before to antraquinone derivatives, such as those of formula (XVI).

The rearrangement of step f) according to the present invention is particularly advantageous, in so far as it allows both the antraquinones derivatives mono-nitrated at position para with respect to the $R_8$ group [i.e. compounds (XVII)A] and those mono-nitrated at position ortho with respect to the $R_8$ [i.e. compounds (XVII)B] group to be converted into the same carboxylic acid of formula (XV), due to the fact that when aromatic mono-nitro compounds are treated with cyanide ions according to the present process, the nitro group is displaced and a carboxyl group enters always ortho to the displaced group.

Further objects of the present invention are represented by the intermediates compounds of formula (XVII)A and (XVII)B before illustrated, and by those of formula (XVII)C and (XVII)D hereinbelow illustrated in the present text.

The process hereinabove described allows rhein derivatives, such as diacerhein, to be obtained in high yields and in very pure form, in particular free from aloe-emodin and from analogues thereof of formula (I) and (XV), wherein —COOH is replaced with —CH$_2$OH.

While the products synthetically obtained by the processes of the prior art always contain at least trace amounts of aloe-amodin, an impurity exerting mutagenic action even in amounts as low as 70 ppm, the presence of which is due to the use of raw materials of natural origin (e.g. extracts of senna leaves, barbaloin), the intermediates and final products obtained by the present processes are totally free from aloe-emodin, which is not therein contained either in ppm or even in ppm fractions, since the present processes exclusively utilizes aloe-emodin free synthetic starting materials, which in no way can give rise to formation of said impurity by means of the steps of the present processes.

Also, this invention further extends to i) compounds selected among the derivatives of formula (I) wherein $R_1$, $R_2$, $R_3$, $R_4$, $R_5$, $R_7$ and $R_8$ are as above defined and $R_6$ is —COOH, and derivatives thereof (i.e. pharmaceutically and cosmetically acceptable esters, amides or ioesters), as well as pharmaceutical compositions for human or veterinary use comprising a therapeutically effective amount of at least one of said compounds combined with at least one pharmaceutically acceptable excipient and/or diluent, and optionally with one or more auxiliary substances, and the cosmetic preparation comprising at least one of said compounds, characterized in that said compounds, compositions and preparations are completely free from aloe-emodin and/or from the derivatives of formula (I), in which R6 is —CH$_2$OH.

The pharmaceutical compositions and cosmetic preparations of the present invention can be prepared by conventional methods.

The present pharmaceutical compositions free from aloe-emodin and analogues thereof of formula (I) wherein $R_6$ is —CH$_2$OH find the same therapeutic application (in particular in human therapy) known for compounds of formula (I) or (XV), e.g. in the treatment of inflammatory states such as those of joints, and are administered at the same unit dosages and daily dosages known for compounds of formula (I) or (XV).

DETAILED DESCRIPTION OF THE INVENTION

As used herein, the alkyl, alkenyl, alkynyl, alcoxy and acyloxy groups typically contain 1 to 20 carbon atoms ($C_1$–$C_{20}$), preferably 1 to 6 carbon atoms ($C_1$–$C_6$). The alkyl groups are typically saturated, straight or branched ones, e.g. methyl, ethyl, n-propyl, isopropyl groups.

The alkenyl and alkynyl groups contain one, or more, preferably one, unsaturation (double or triple bonds).

The alkenyl is e.g. a —CH$_2$CH=CH$_2$ allyl group.

The alcoxy and acyloxy groups are typically —OCH$_3$ and —OCOCH$_3$.

As used herein, the aromatic groups, optionally present in the various substituents from $R_1$ to $R_8$ of the anthraquinone structure may be carbocyclic or heterocyclic, mono- or polycyclic, and preferably contain 5- or 6-membered rings (cycles).

The carbocyclic aromatic groups are, for example, a phenyl group, optionally substituted or fused with another carbocyclic or heterocyclic group, with 5 or 6 atoms in the cycle, either carbocyclic (e.g. naphthyl) or heterocyclic.

Heterocyclic aromatic groups are typically heterocycles with 5 or 6 membered rings, containing one or more (preferably 1 to 3) heteroatoms selected out of O, N and S, optionally fused or substituted with another carbocyclic or heterocyclic aromatic ring as defined above.

Examples of aromatic heterocycles are oxazole, thiazole, imidazole, optionally fused with a phenyl, e.g. benzoimidazole.

Furthermore, the aforesaid alkyl and aromatic groups may optionally be substituted, e.g. with alcoxy, phenoxy, vinyl or halogen groups.

The arylalkyl group is an alkyl group substituted with one or more aromatic groups as defined above, and is preferably benzyl, $C_6H_5$—$CH_2$—.

Out of the rhein derivatives indicated above as new, the preferred ones are those of formula (I), in which $R_7$ is H and $R_3$ is an —ORh or —OCORh group, where Rh is H, an alkyl or aromatic group (excluded the compounds already disclaimed in the Summary), also referred to herein as compounds (I)A; out of compounds (I)A, particularly preferred are the ones in which $R_1$, $R_8$ and $R_3$ are different from —OH and are preferably —ORa, —ORb or —ORh groups, respectively, where Ra, Rb and Rh are preferably $C_1$–$C_3$ alkyl groups.

Out of the rhein derivatives indicated as new in the Summary hereinabove, are further preferred the ones in which $R_3$ is H and $R_7$ is an alkyl, alkenyl, alkynyl or arylalkyl group, also referred to herein as compounds (I)B.

Out of the present new derivatives (I) or (I)A or (I)B, preferred are the ones in which:

$R_1$ is —OH or —ORa or —OCORa, and $R_8$ is —OH or —ORb or —OCORb, where Ra and Rb, which may be the same or different one from another, each represents H or a $C_1$–$C_6$ alkyl group, e.g. Ra or Rb are —$CH_3$, —$CH_2CH_3$, —$(CH_2)_2CH_3$ and —$CH(CH_3)_2$;

$R_6$ is —OCORC, —CONRdRe, —$CH_2$OCORf or —$CH_2$ORg, where Rc and Rd, Re and Rf are H or a $C_1$–$C_6$ alkyl group, and preferably are H, —$CH_3$, or —$CH_2CH_3$, and Rg is a $C_1$–$C_6$ alkyl group, preferably —$CH_3$;

$R_3$ is H or —ORh or —OCORh, where Rh is H or a $C_1$–$C_6$ alkyl group, preferably —$CH_3$;

$R_7$ is selected out of the group consisting of H, $C_1$–$C_6$ alkyl, $C_1$–$C_6$ alkenyl (preferably allyl —$CH_2CH$=$CH_2$); and arylalkyl, preferably benzyl.

An example of preferred compound of formula (I)A is represented by compound D1: compound of formula (I), in which $R_2$=$R_4$=$R_5$=H; $R_7$=H; $R_1$=$R_3$=$R_8$=—$OCH_3$, and $R_6$=—COOH.

Examples of preferred compounds of formula (I)B are as follows:

D2: compound of formula (I), in which $R_2$=$R_4$=$R_5$=H, $R_3$=H, $R_1$=—$OCH(CH_3)_2$, $R_6$=—$COOCH_2CH_3$, $R_7$=—$(CH_2)_2CH_3$ and $R_8$=—OH;

D3: compounds of formula (I), in which $R_2$=$R_4$=$R_5$=H, $R_1$=—O—CO—$CH_3$, $R_3$=H, R6=—CONH$R_b$, where $R_b$ is $C_1$–$C_3$ alkyl; $R_7$ is $C_3$–$C_5$ alkyl; and $R_8$=—OH;

D4: compound of formula (I), in which $R_2$=$R_4$=$R_5$=H, $R_1$=—OH, $R_3$=H, $R_6$=—$COOCH_3$, $R_7$ is $CH_2CH$=$CH_2$, and $R_8$=—OH;

D5: compound of formula (I), in which $R_2$=$R_4$=$R_5$=H, $R_1$=—OH, $R_3$=H, $R_6$=—COOH, $R_7$ is —$CH_2$Ph, where Ph is phenyl, and $R_8$=—OH;

D6: compound of formula (I), in which $R_2$=$R_4$=$R_5$=H, $R_1$=—$OCOCH_3$, $R_3$=H, $R_6$=—$CH_2$OCO—$CH_3$, $R_7$ is —$CH_3$, and $R_8$=—$OCOCH_3$;

D7: compound of formula (I), in which $R_2$=$R_4$=$R_5$=H, $R_1$=—$OCH_3$, $R_3$=H, $R_6$=—COOH, $R_7$ is —$CH_2$Ph, where Ph is phenyl, and $R_8$=—OH.

The new derivatives of formula (I) according to the present invention can be administered by various ways, e.g. by the oral, rectal, topical or parenteral way, e.g. by injection or infusion, to man and animals, in particular to man.

The new rhein derivatives of formula (I) can be administered as such or in the form of pharmaceutical compositions including a therapeutically effective amount of at least a rhein derivative of formula (I) [as defined above for the new rhein derivatives of the invention], a salt thereof or a pharmaceutically acceptable derivative thereof, in combination with one of more pharmaceutically acceptable excipients.

The excipient can be solid or liquid, e.g. a diluent or a solvent.

Said compositions are prepared by conventional techniques, well known in the pharmaceutical art, as reported e.g. in Remington's Pharmaceutical Science, 18th Ed., 1990.

For example, the new rhein derivatives of formula (I) claimed herein can be mixed, diluted and/or included in a carrier, which can be solid, semisolid or liquid, and enclosed, e.g. into capsules (such as soft or hard gelatin capsules), sachets, or other containers.

The composition can also be in the form of tablets, pills, capsules, elixirs, suspensions, syrups, aerosols, unguents or oitments, containing e.g. up to 10% by weight of active ingredient, suppositories, preparations for injection in the form of solutions, suspensions or powders manufactured in sterile form.

Examples of carriers are lactose, dextrose, sccharose, sorbitol, mannitol, starch, acacia gum, calcium phosphate, alginates, tragacanth, gelatin, methylcellulose, methyl- and propyl-parabens, talc, magnesium stearate, and mineral oil.

The preparations for injection can be also formulated according to methods known to the art in forms providing immediate, controlled or delayed release of the active ingredient.

The present compositions contain the active ingredient in a therapeutically effective amount. In the compositions formulated as a combination of unit doses, each unit dose preferably contains from about 5 mg to about 500 mg, e.g. from 25 mg to 200 mg of active ingredient.

The new rhein derivatives of the invention are effective when administered within a wide range of daily doses, which depends on various factors, such as the type of disease, the patient's state, the way of administration, the single active ingredient selected, e.g. in quantities ranging about from 0.5 to 300 mg/kg, more usually from 5 to 100 mg/kg bodyweight/day.

The $R_A$, $R_B$, $R_C$, and $R_D$ groups present in the various chemical intermediates referred to in the present application may be varied, depending on the requirements, from one step to the other of the present processes, by means of known methods.

Preferably, the reaction mixture obtained from diazotisation (step b') is directly subjected to step b") without prior isolation of the diazo derivative intermediate.

Removal of the $R_A$ group through step c) is preferably carried out on the compound of formula (IV) obtained in step b"), in which $R_A$ is a protective group as defined above, after performing successively steps a), b') and b"): derivatives of formula (I), in which $R_1$ is —OH, are thus obtained.

Preferably, $R_A$ is a protective group removable under acid conditions, in particular a $C_1$–$C_4$ alkyl, such as $CH_3$, and step c) is acid hydrolysis, e.g. by treatment with HBr.

The derivatives of formula (I), in which $R_1$=$R_8$=OH, are preferably obtained from the corresponding derivatives of formula (II), in which $R_A$ is a protective group, in particular an alkyl group, preferably a $C_1$–$C_4$ alkyl, by steps a) and b) as defined above and by subjecting the corresponding intermediate of formula (IV) to a deblocking step (step c).

Alternatively, the derivatives of formula (I), in which $R_1=R_8=$OH, can be obtained from the diarylketone of formula (II), in which $R_A$ is H, through steps a) and b). In this case, the resulting compound of formula (IV) corresponds to the compound of formula (V), which may be converted into the desired compound of formula (I).

The compounds of formula (I), in which $R_1$ is —ORa (different from —OH) or —OCORa, and typically $R_1$ is —$OR_a$, in which Ra is an alkyl or aromatic group, are preferably prepared through the compounds of formulas (II), (III), (IV), (VI), (VII), (VIII), (IX), (X), and (XI), in which —$OR_A$ has the meaning corresponding to $R_1$. Thus the compounds of formula (I), in which $R_1$ is different from —OH, and $R_8$ is —OH may be advantageously obtained.

Acylation or etherification [steps d) and d')] described above are preferably carried out on the compounds of formula (I), in which $R_1$, $R_2$ or both are —OH, or on the compounds of formula (V), to give the derivatives of formula (I), in which $R_1$, $R_8$ or both are acyl groups —OCORa and —OCORb, as defined above, or ether groups —ORa or —ORb, as defined above, where Ra and Rb are different from H.

The compounds of formula (III), in which $R_B$ is —OH, can be converted into the corresponding compounds of formula (III), in which $R_B$ is different one from another from —OH, and is e.g. —ORc, —NRdRe or —SRf, by conventional methods, e.g. by treatment with an alcohol RcOH (Rc different from H), in the presence of an acid catalyst, or by treatment of compound (III) with RdReNH or RfSH, in which $R_B$ is —OH or —ORc, where Rc is different from H.

Conversion of the derivatives of formula (II) or (III) wherein $R_B$ is different from —OH into the corresponding derivatives (II) or (III) wherein $R_B$ is —OH typically takes place in an aqueous acid medium, during steps b') and/or b''), in particular b''), giving the phenol derivative of formula (IV) having a free carboxylic function; or, alternatively, said conversion may be obtained through a further hydrolysis, either acid or basic.

In the present process, the compounds of formula (II), in which $R_C$ is H and $R_B$ is —OH, are preferably used: among them, particularly preferred are the ones in which $R_A$ is Ra, where Ra is typically a $C_1$–$C_4$ alkyl.

Particularly preferred for the purposes of the present invention are the compounds of formula (II), in which $R_C=$H, $R_B=$OH and $R_2$, $R_3$, $R_4$, $R_5$, and $R_7$ are as defined for the compounds of formula (I) and $R_A$ is a protective group of the —OH function. Among them, particularly preferred are the ones in which $R_A$ is —Ra or —CORa and still more preferred are the ones in which $R_A=$Ra, where Ra is a $C_1$–$C_4$ alkyl, e.g. —$CH_3$, or —$CH(CH_3)_2$.

Still more preferred are the compounds of formula (II), in which $R_C$ is H, $R_B$ is OH, $R_2=R_4=R_5=$H and at least one out of $R_3$ and $R_7$ is different from H, and is as defined above for the aforesaid new rhein derivatives of formula (I), more particularly those wherein:

$R_3$ is H, an —ORh or —OCORh group, where Rh is H or an alkyl or aromatic group, more particularly Rh is H or $C_1$–$C_4$ alkyl, preferably. —$CH_3$;

$R_7$ is H, alkyl, alkenyl, alkynyl or arylalkyl group, being preferably selected out of H, $C_1$–$C_6$ alkyl (e.g. —$CH_3$, $C_3$–$C_5$ alkyl, —$(CH_2)_2CH_3$), $C_1$–$C_6$ alkenyl (more preferably an allyl, —$CH_2CH=CH_2$); and arylalkyl, more preferably benzyl.

Out of the last ones, particularly preferred are the compounds of formula (II), in which $R_3=$H and $R_7$ is as defined above, and the ones in which $R_7=$H and $R_3$ is as defined above.

Particularly preferred for the purposes of the present invention are the compounds of formulas (III), (IV) or (V), whose substituents [$R_A$, $R_B$, $R_2$, $R_3$, $R_4$, $R_5$, and $R_7$ for the compounds of formula (III); $R_A$, $R_2$, $R_3$, $R_4$, $R_5$, and $R_7$ for the compounds of formula (IV) and $R_2$, $R_3$, $R_4$, $R_5$, and $R_7$ for the compounds of formula (V)] are as defined for the compounds of formula (II) hereinabove referred to as preferred (or particularly preferred).

The strong concentrated acids suitable for the conversion of diarylketone of formula (II) to the 1-anthraquinone derivative of formula (III) according to the present invention are for instance either mineral (inorganic) or organic acids, such as sulphuric acid and $CF_3SO_3H$.

For the purposes of the present invention, concentrated acids are either acid solutions, e.g. acid solutions in water, with an acid concentration of about at least 90% weight by weight, e.g. of about 95%–98% weight by weight (w/w), or superacids.

In present step a), superacids such as fuming sulphuric acid ($H_2SO_4.SO_3$, also known as oleum, with variable amount of $SO_3$) or $CF_3SO_3H$ can be used, or concentrated sulphuric acid (e.g. about 95%–98% w/w).

More particularly, concentrated sulphuric acid or $CF_3SO_3H$ can be used, more preferably $CF_3SO_3H$.

Step a) is for instance carried out at a temperature approximately ranging from 0° C. to 250° C., preferably from 100° C. to 200° C., and more preferably from about 140° C. to 160° C.

For example, the diarylketone of formula (II) and the strong concentrated acid (e.g. a superacid) are mixed under stirring at a temperature ranging from 0° C. to room temperature (about 20° C. to 30° C.); then the temperature is gradually raised to a value preferably ranging from about 100° to about 200° C., typically from about 140° C. to 160° C.

The diarylketone of formula (II)/concentrated acid ratio typically ranges from 0.5:1 to 4.75:1, e.g. about 1:3, expressed as mmol of product (II) per ml of concentrated acid.

The product of formula (III) is isolated by conventional methods: in particular, it precipitates from the reaction medium generally in the form of crystals, after neutralization with a strong base, e.g. NaOH, which is preferably added at a low temperature, e.g. 4° C. to 8° C.; then it is separated from the liquid phase by conventional methods, e.g. filtration.

Diazotisation (step b') is preferably carried out by treatment with nitrous acid, in an aqueous medium; the reaction temperature preferably ranges from 0° C. to 8° C., e.g. from about 0° C. to 5° C.

Nitrous acid is preferably generated in the reaction medium by the action of a strong acid (e.g. an inorganic acid, such as $H_2SO_4$, or an organic acid, such as $CF_3SO_3H$, preferably $H_2SO_4$) on a nitrite, typically an alkali metal nitrite, such as $NaNO_2$.

For example, step b') is carried out with $NaNO_2$, in a concentrated $H_2SO_4$/water mixture in a ratio ranging from 1:1 to 1:3 (v/v=volume/volume).

The diazotising agent is typically used in molar excess with respect to the compound of formula (III), e.g. in a quantity ranging from about 1.1 to 2.0 mol, preferably of about 1.5 mol per mol of (III).

The diazotised intermediate of formula (VI)

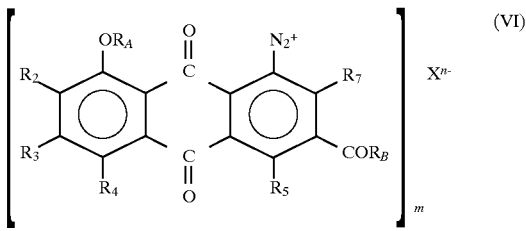

in which $R_A$, $R_B$, $R_2$, $R_3$, $R_4$, $R_5$, $R_7$ are as defined for the compounds of formula (I), X is the strong acid anion (in whose presence diazotisation is carried out);

n is the number corresponding to the number of negative charges of said anion;

when $R_B$ is H, m is (n−1), or, when $R_B$ is different from H, m=n, can be isolated from the reaction medium of diazotisation (step b'), e.g. by filtration.

The diazo derivative of formula (VI) is preferably the one in which $R_B$ is —OH, and $R_A$ is a protective group of the —OH function and in which $R_A$, $R_2$, $R_3$, $R_4$, $R_5$, and $R_7$ are as defined for the derivatives of formula (II) referred to in the present text as preferred or particularly preferred; furthermore, preferably X is $SO_4^{2-}$ (n=2) and m is 1.

In step b", the strong acid is e.g. an inorganic acid, such as sulphuric acid, or an organic acid, such as $CF_3SO_3H$; sulphuric acid is typically used.

Step b") is carried out at a temperature generally ranging from 100° C. to 250° C., preferably from 140° C. to 150° C.

Under typical conditions, the reaction medium of steps b') and b") is a strong acid:water mixture in a ratio preferably ranging from 1:0.5 to 1:5 (v/v), more preferably from 1:1 to 1:3 (v/v).

Furthermore, steps b') and b") are preferably carried out with substrate of formula (III), (IV) or (VI)/reaction medium (typically a strong acid/water mixture) ratios ranging from 1:0.5 to 1:5, typically of 1:3, expressed as mmol of the substrate of formula (III), (IV) or (VI) per ml of reaction medium.

As mentioned above, step b") is preferably carried out directly on the reaction mixture coming from step b'). For example, diazotisation is carried out in an aqueous acid medium; then the reaction mixture from step b'), optionally diluted with an additional strong acid/water mixture, is heated to the temperature of step b").

The resulting phenol derivative of formula (IV) is easily isolated from the acid reaction mixture by cooling to room temperature, followed by separation of the precipitate so obtained, e.g. by filtration.

Acid hydrolysis as per step c) is e.g. carried out at a temperature ranging from about 90° C. to about 160° C., more preferably from about 100° C. to about 120° C. Step c) is typically a step meant for the removal of group $R_A$=alkyl, and is preferably carried out with concentrated HBr (about 48% w/w HBr aqueous solution), preferably in glacial acetic acid as diluent (e.g. in a quantity of about 5 to 20 ml/mmol substrate); the temperature is preferably the reflux temperature of the reaction mixture.

The quantity of concentrated HBr ranges, e.g., from about 0.1 ml to 10 ml, typically from 0.5 ml to 3 ml concentrated HBr per mmol of substrate of formula (II), (III) or (IV).

The reaction product from step c) generally precipitates in the reaction medium at room temperature, wherefrom is separated, e.g. by filtration; then it is preferably purified by crystallization, e.g. from an alcohol, such as methanol.

The reactions as per steps a), b'), b"), and c) described above are completed within short times, generally ranging from about 15 min to 2–3 h, and give the corresponding highly pure products in high yields.

Treatment with the acylating agent as per step d) is carried out at temperatures preferably ranging from about 50° C. to about 100° C., e.g. from about 70° C. to 90° C.

The acylating agent is, e.g., the anhydride or acyl halide of the acid $R_aCOOH$, where $R_a$ is as defined above, e.g. acetic anhydride, an acetyl halide (e.g. a chloride), or hexachloroacetone.

Typically, the halide is used in the presence of a base as protons acceptor, and the anhydrides are used in the presence of an acid or of a base as a catalyst.

The acid may be, e.g., acetic acid, methanesulphonic acid, trifluoromethanesulphonic acid, concentrated sulphuric acid, preferably $H_2SO_4$, and the base may be e.g. sodium acetate or $NaHCO_3$.

Preferably, acetic anhydride in glacial acetic acid is used as a reaction solvent (in a quantity e.g. ranging from about 0.5 to about 5 ml per mmol of substrate to be acylated, in the presence of a catalytic amount of conc. $H_2SO_4$ The acylating agent is generally used in a stoichiometric excess with respect to the —OH groups to be acylated, e.g. in amounts from 2.0 to 5.0 mol, preferably to 3 mol per mol of substrate.

The resulting acylated derivatives generally precipitate by cooling to room temperature and are then separated by conventional methods, such as filtration.

The diarylketones of formula (II) are novel products, and were synthesized by the Applicant from known and commercially available compounds or in any case prepared by conventional methods.

Substituents $R_2$, $R_3$, $R_4$, $R_5$, or $R_7$, when different from H, may be inserted in the aromatic rings at various steps of the synthesis, prior to treatment of the diphenylketone of formula (II) with a superacid according to step a); for example, said substituents may be inserted by conventional substitution reactions of the aromatic ring on unsubstituted reaction intermediates, corresponding to the compounds of formula (XIII), (XIV), (VII), (VIII), (IX), (X), (XI), (II)A or (II), in which at least one of $R_2$, $R_3$, $R_4$, $R_5$ and $R_7$ is H.

The derivative of formula (VII) is obtained, e.g., by oxidazing a dimethylbenzene derivative of formula (XII)

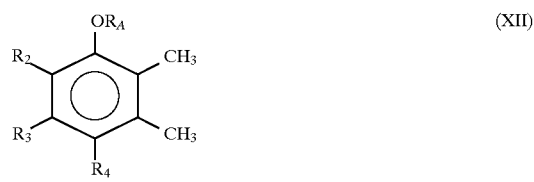

in which $R_A$ is a protective group of the —OH function, preferably a saturated, straight or branched $C_1$–$C_4$ alkyl group, and $R_2$, $R_3$, $R_4$ are as defined for the corresponding derivatives of formula (I), by treatment with an oxidizing agent, preferably a hypochlorite (such as NaClO), and with an alkyl halide, preferably containing 1 to 6 carbon atoms (such as n-butylbromide), in the presence of a transition metal salt (preferably a RU(III) salt, such as $RuCl_3$), preferably operating in an aqueous medium, at alkaline pH, at a temperature preferably ranging from 30° C. to 100° C., e.g. from 40° C. to 60° C.

The oxidation of the compound of formula (XII) is generally carried out in water, preferably at a pH of about, this value being maintained by addition of a strong base, such as NaOH.

Preferably, with respect to the derivative of formula (XII), the oxidant is used in amounts of 2 to 5 mol, e.g. 3 mol; the halide is used in a stoichiometric amount, the catalyst is used typically in an amount ranging from 1% to 30% by mol, preferably from 10% to 25% by mol.

Several derivatives of formula (XII) are commercially available or, in any case, can be prepared by conventional methods, e.g. by known methods of substitution of the aromatic nucleus, on derivatives of formula (XII), in which $R_2=R_3=R_4=H$ and $R_A$ is a protective group of the —OH function, preferably a $C_1$–$C_4$ alkyl group.

In steps 1), 2), 3), and 4) of the process for the preparation of diarylketones of formula (II)A, $R_A$ is preferably a $C_1$–$C_4$ alkyl group, in particular methyl.

For the purposes of the present invention, the preferred derivatives of formula (VII) are the ones in which $R_A$ is —Ra or —CORa, and especially $R_A$=Ra, where Ra is a $C_1$–$C_4$ alkyl group, e.g. —$CH_3$, —$CH(CH_3)_2$, preferably $CH_3$, and $R_2$, $R_3$ and $R_4$ are as defined for the desired compounds of formula (I) to be prepared and, in particular, for the compounds of formula (II) referred to herein as preferred.

Out of them, particularly preferred are the derivatives of formula (VII), in which $R_2=R_4=H$, and $R_3$ is H, an —ORg, or —OCORg group, where Rg is H, an alkyl or aromatic group, more particularly Rg is H or a $C_1$–$C_4$ alkyl group, preferably —$CH_3$.

Out of the derivatives of formula (VIII) and of formula (IX), particularly preferred are the ones in which $R_A$, $R_2$, $R_3$, and $R_4$ are as defined for the compounds of formula (VII) [or of formula (II) hereinabove referred to as preferred ones; furthermore, preferred compounds of formula (VIII), are the ones in which $R_C$ is a $C_1$–$C_4$ alkyl group, more preferably —$CH_3$; preferred compounds of formula (IX) are the ones in which $R_C$ is a $C_1$–$C_4$ alkyl group, more preferably —$CH_3$, and Hal is Cl or Br, more preferably Cl.

Preferred derivatives of formula (X) are the ones in which $R_B$ is —ORa, where Ra is a $C_1$–$C_4$ alkyl group, preferably $CH_3$; $R_D$ is a $C_1$–$C_4$ alkyl group, preferably $CH_3$; and $R_5$ and $R_7$ are as defined for the desired compounds of formula (I) to be prepared or for the compounds of formula (II) referred to herein as preferred ones Further preferred are the compounds of formula (X) in which $R_5$ is H and $R_7$ is H, an alkyl, alkenyl, alkynyl or arylalkyl group, being preferably selected out of H, $C_1$–$C_6$ alkyl (e.g. —$CH_3$, $C_3$–$C_5$ alkyl, —$(CH_2)_2CH_3$), $C_1$–$C_6$ alkenyl (preferably allyl, —$CH_2CH=CH_2$), and arylalkyl, (preferably benzyl).

Preferred derivatives of formula (XI) are the ones in which $R_A$, $R_2$, $R_3$, $R_4$, and $R_D$, $R_B$, $R_7$, $R_5$ are as defined for the compounds of formulas (X) and (IX) referred to herein as preferred, or for the compounds of formula (II) referred to herein as preferred.

Preferred derivatives of formula (II)A are the ones in which $R_A$, $R_2$, $R_3$, $R_4$, $R_5$, and $R_7$ are as defined for the compounds of formula (XI) or of formula (II) referred to herein as preferred. Further preferred derivatives of formulas (XI) and (II)A are the ones in which at least $R_3$ or $R_7$ is different from H.

The temperature of step 1) preferably ranges from about 30° C. to 100° C., typically from about 50° C. to 70° C.

Furthermore, $R_COH$ is preferably $CH_3OH$ and is preferably used as reaction solvent [e.g. 0.5–2 ml solvent per mmol substrate (VII)].

Preferably, the Cu(I) salt is a halide, such as CuCl, and the acid is an inorganic strong acid, typically a hydrogen halide acid, such as HCl; furthermore, the Cu(I) salt and the acid are preferably used in a stoichiometric amount with respect to the compound of the formula (VII), as well as up to 2 mol per mol of (VII).

The temperature of step 2) preferably ranges from about 50° C. to 120° C., more preferably from about 60° C. to 90° C.; the halogenating agent is, e.g., thionyl chloride or $PCl_5$ or $PCl_3$.

Typically, thionyl chloride is used, e.g., as a reaction medium [e.g. from 1 to 2 ml per 100 mmol of the derivative of formula (VIII)], preferably at the reflux temperature of the reaction mixture (78° C. to 80° C. about).

The temperature of step 3) preferably ranges from about 40° C. to 100° C., more preferably from about 40° C. to 60° C.

Furthermore, the catalyst is selected out of the catalysts commonly used in Friedel-Crafts alkylations or acylations and is typically an aluminium halide, such as $AlCl_3$.

Step 3) preferably utilizes stoichiometric ratios between the derivatives of formulas (X) and (IX) and amounts of Friedel-Crafts catalyst typically ranging from 0.1% to 10% by mol, more typically from about 1% to 2% by mol with respect to the derivative of formula (IX).

According to a preferred embodiment, step 3) is carried out in the absence of solvents, by mixing the substrates of formulas (IX) and (X) with the catalyst, and raising the reaction temperature to the selected value.

Steps 2) and 3) may also be carried out in the presence of diluents or inert organic solvents.

In the hydrolysis (step 4), the temperature preferably ranges from 30° C. to 100° C. and more preferably is of about 80° C. Furthermore, the base is preferably an alkaline hydroxide, such as NaOH, used in a quantity preferably ranging from about 0.5 to 1 mol per mol of compound of formula (XI).

Step 4) is preferably carried out in a water-alcohol mixture (the alcohol being, e.g., methanol, or ethanol) e.g. in a 50:50 v/v water/ethanol mixture.

Once the reaction has been completed, diarylketone (II)A is recovered from the reaction medium by acidification, typically with HCl.

The derivatives of formula (X), in which $R_B$ is —NRdRe, —SRf or —OH, can be obtained from the corresponding derivatives of formula (X), in which $R_B$ is —ORc, by conventional methods.

The derivatives of formula (X), in which $R_B$ is —ORc, where Rc is an alkyl or aromatic group, are typically obtained by esterification of a 3-aminobenzoic acid derivative of formula (XIV)

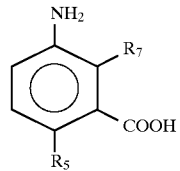

(XIV)

in which $R_5$ and $R_7$ are as defined for the compounds of formula (I) to be prepared, followed by acylation of the amino function.

For example, said 3-aminobenzoic acid derivative (XIV) is treated with an $R_BOH$ alcohol, where $R_B$ is an alkyl or aromatic group, preferably a $C_1$–$C_4$ alkyl group, such as $CH_3$, in the presence of an acid catalyst, preferably at a temperature ranging from 30° C. to 100° C., e.g. from 50° C. to 70° C., to give the corresponding ester of formula (XIII)

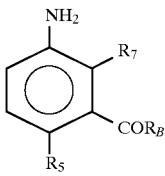
(XIII)

in which $R_B$ is as defined above and more preferably is $CH_3$.

$R_BOH$ is preferably an alkyl, $CH_3OH$, and is typically used as a reaction solvent; furthermore, the acid catalyst is, e.g., concentrated $H_2SO_4$, in a quantity ranging from 1 to 5 ml, e.g. 3 ml, per 100 mmol of substrate.

The resulting derivative of formula (XIII) is treated with an acylating agent, preferably with the anhydride of the acid $R_DCOOH$ (preferably acetic anhydride), where $R_D$ is as defined above and is preferably a saturated $C_1$-$C_4$ alkyl group, typically —$CH_3$, preferably in the presence of an acid catalyst, such as the acid $R_DCOOH$ (e.g. acetic acid), at a temperature preferably ranging from about 80° C. to about 120° C., more preferably from about 100° C. to 120° C.

The anhydride and the acid are used, for instance as solvents, e.g., in an amount of about 2 to 10 ml acid, and from 1 to 2 ml anhydride per 100 mmol of substrate (XIII).

The compounds of formula (X) can be, in any case, prepared by other conventional methods.

According to a particular embodiment of the present invention, compounds of formula (X) wherein $R_B$ is $OR_C$, and $R_C$ is alkyl or aromatic group can be prepared by subjecting 3-aminobenzoic acid [compound (XIV) wherein $R_5$=$R_7$=H] to esterification and to acylation of the amino group, thus affording the corresponding compound (X) wherein $R_5$=$R_7$=H, which is them converted into the corresponding compound (X) wherein at least one of $R_5$ and $R_7$ is different from H by means of conventional techniques.

According to a preferred embodiment of the present process via mono-nitration followed by treatment with cyanide ions, step e) hereinabove illustrated is carried out on antraquinone derivative of formula (XVI) wherein $R_1$ and $R_8$ are as above defined in step e), and $R_2$=$R_3$=$R_4$=$R_5$=$R_7$=H, hereinbelow represented as compound of formula (XVI) A,

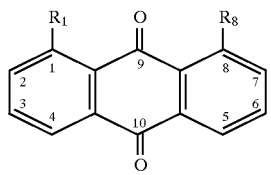
(XVI)A wherein $R_1$ and $R_8$ are as above defined in step e), affording the corresponding compound of formula (XVII)A and (XVII)B, wherein $R_1$ and $R_8$ are as above defined in step e) and $R_2$, $R_3$, $R_4$, $R_5$ and $R_7$ are H, hereinbelow represented with formulas (XVII)C and (XVII)D

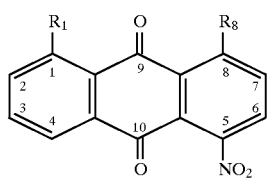
(XVII)C

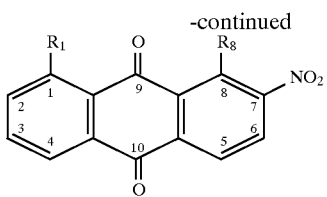
(XVII)D wherein $R_1$ and $R_8$ are as above defined in step e), which are then converted by means of step f) into the corresponding carboxylic acid of formula (XV), wherein $R_1$ and $R_8$ are as above defined in step e), and $R_2$=$R_3$=$R_4$=$R_5$=$R_7$=H, hereinbelow represented with formula (XV)A

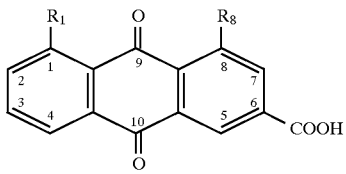
(XV)A wherein $R_1$ and $R_8$ are as above defined in step e).

According to a preferred embodiment of the present invention, mono-nitration according to step e) is carried out on substrate (XVI) or (XVI)A wherein $R_1$ and $R_8$ are —O—acyl groups —OCORa and —OCORb, wherein Ra and Rb are as above defined for step e), and are preferably $C_1$-$C_4$ alkyl groups, more preferably —$CH_3$ groups, and more particularly Ra=Rb, affording by means of step e) the corresponding derivatives of formula (XVII)A, (XVII)B or mixtures thereof, or more particularly (XVII)C, (XVII)D or mixtures thereof, and then by means of step f) the corresponding derivatives of formula (XV) or more particularly (XV)A, wherein $R_1$ and $R_8$ have the same meaning.

The above illustrated process is in particular suitable for the preparation of diacerhein [compound of formula (XV)A wherein $R_1$=$R_8$=—$OCOCH_3$], which is obtained by means of steps e) and f) through the corresponding derivatives of formula (XVI)A, (XVII)C and/or (XVII)D, wherein $R_1$ and $R_8$ have the same meaning.

Acyl derivatives of formula (XVI) or (XVI)A wherein $R_1$ and $R_8$ are —O—acyl groups as above defined can be easily obtained treating the corresponding derivatives wherein $R_1$ and $R_8$ are —OH with the corresponding acylating agent, e.g. under the working conditions as per step d) hereinabove described.

According to a preferred embodiment of the present invention, compounds of formula (XVI) or (XVI)A wherein $R_1$=$R_8$=—$OCOCH_3$ are obtained by treating the corresponding 1,8 dihydroxyanthraquinones [i.e. compounds of formula (XVI) or (XVI)A wherein $R_1$=$R_8$=—OH] with acetic anhydride (more preferably used in excess, as reaction medium), in the presence of sodium acetate as the catalyst, at temperatures about of from 80° C. to 100° C., e.g. at about 90° C.–95° C. Some compounds of formula (XVI) or (XVI)A, such as 1,8-dihydroxyanthraquinone (crysazin, danthron), i.e. compound of formula (XVI)A wherein $R_1$=$R_8$=H are commercially available.

Other compounds of formula (XVI) can be prepared from compound of formula (XVI) wherein substituents $R_2$, $R_3$, $R_4$, $R_5$, and $R_7$ are H, by replacing by means of conventional techniques said substituents with the functional groups $R_2$, $R_3$, $R_4$, $R_5$ or $R_7$ different from H. Alternatively, compounds of formula (XVI) or (XVI)A can be prepared according to a process analogous to steps 1) to 4) hereinabove described for the preparation of compounds of formula (I), passing through the corresponding intermediates of formula (II), (II)A, (III), (IV), (V), (VI), (VII), (VIII), (IX), (X), (XI), (XII) and (XIII) and (XIV), wherein $R_5$ and optionally $R_7$ are H, and the substituent at position 6 according to the same ring numbering used in the present text (i.e. R6 or the —COOH group) is also H.

In step e) of the present process, the essentially stoichiometric amount of nitric acid ranges from a slight molar defect to a slight molar excess of nitric acid with respect to the substrate to be nitrated.

In particular, mono-nitration according to step e) is preferably carried out with molar ratios nitric acid:substrate (XVI) or (XVI)A preferably comprised from about 0.8:1 to about 1.2:1. Preferably, nitric acid is used in a rather slight defect with respect to the substrate of formula (XVI) or (XVI)A: more preferred nitric acid: substrate molar ratios range from about 0.8:1 to about 1.0:1, further preferably from about 0.85:1 to about 0.95:1.

Mono-nitration according to step e) is preferably carried out in diluted solutions of nitric acid in sulphuric acid, typically in concentrated sulphuric acid, preferably containing at least 90% w/w (weight/weight) of $H_2SO_4$ in water, more particularly about 95%–98% w/w of $H_2SO_4$ in water.

The nitric acid concentration in the reaction medium of step e) preferably varies from nitric acid:sulphuric acid volume by volume ratios comprised from 1:1000 to 1:30 volume/volume (v/v), referred to pure $HNO_3$ (i.e. essentially 100% $HNO_3$) and concentrated $H_2SO_4$.

Mono-nitration according to step e) is preferably carried out at a temperature comprised between −50° C. and +5° C., more preferably at about −40° C.

In step e), substrate concentration in the reaction medium typically ranges from 1.10 to 1:1, more typically from 1:2.5 to 1:3.5, expressed as ratio between the weight (grams) of substrate (XVI) or (XVI)A and the volume (milliliters) of diluent, more particularly the nitric acid/sulphuric acid mixture.

In step f), the cyanide ions source is typically an alkaline or alkaline-earth cyanide, such as NaCN.

The reaction temperature of step f) is for instance comprised between +20° C. and +100° C., more preferably from about +40° C. to about 60° C.

In step f), the cyanide ions are typically added in a stoichiometric excess with respect to the reaction substrate (mono-nitro anthraquinone derivative), for instance in molar ratios cyanide:substrate ranging from about 20:1 to 5:1, more preferably from about 12:1 to 10:1 (wherein the substrate corresponds to the mono-nitro derivative of formula (XVII)A, (XVII)B or mixture thereof, or more particularly to the mono-nitro derivative of formula (XVII)C, (XVII)D or mixture thereof.

Step f) is typically carried out in aqueous medium, for instance in water, optionally admixed with a co-solvent suitable for solubilizing the substrate, for instance a ether type-cosolvent such as tetrahydrofuran, or in any case a solvent with a dielectric constant $\in$(20° C.) of at least about 20, e.g. between 20 to 40, such as an alcohol (e.g. methanol, ethanol).

For instance, tetrahydrofuran: water mixtures in ratios about of from 50:50 to 10:90, e.g. about 20:80 v/v are used. Step f) is carried out at an approximately neutral pH.

In step f), the concentration of substrate in the reaction medium corresponds for instance to weight:volume ratios (in grams:milliliters) of substrate of formula (XVII) or (XVII)A to solvent about of from 1:20 to 1:1, more typically from 1:12 to 1:8.

The process of the present invention as per step e) and d) is also advantageous for the preparation of the pharmacologically active rhein derivatives of formula (I) hereinabove indicated as new in the present text, which can be obtained mono-nitrating according to step e) derivatives of formula (XVI) wherein $R_1$, $R_2$, $R_3$, $R_4$, $R_5$, $R_7$ and $R_8$ are as defined for the aforementioned new rhein derivatives of formula (I), provided that at least one of $R_5$ or $R_7$ is H, then subjecting the corresponding mono-nitro derivatives of formula (XVII) A, (XVII)B or mixtures thereof, or (XVII)C, (XVII)D or mixture thereof thus obtained to rearrangement by treatment with cyanide ions according to step f).

The following examples are conveyed by way of indication, not of limitation, of the present invention.

Method A: Preparation of phthalic acid derivative of formula (VII) [where $R_A$ is a protective group of the —OH function]

The following mixture was prepared:

0.1 mol of derivative of formula (XII), in which $R_A$ is a protective group of the —OH function, was added with 0.3 mol NaClO, as an aqueous solution containing 15% active Cl, 0.1 mol n-butylbromide, 0.02 mol $RuCl_3.3H_2O$.

The mixture was stirred vigorously at 50° C. and the solution pH was maintained at 8–9 by addition of 2M NaOH.

When the pH of the solution remained constant, the reaction mixture was allowed to stir for an additional 1 h, cooled to room temperature and acidified with a conc. HCl—$H_2O$ mixture until complete precipitation of methoxyphthalic acid. The precipitate was collected by filtration and dried under reduced pressure. The yield generally ranged from 90% to 98%.

Method B: Preparation of the derivative of formula (X) [$R_C$=$OCH_3$, $R_D$=$CH_3$, $R_5$ and $R_7$ are as defined for the desired derivatives of formula (I)]

a) Preparation of the derivative of formula (XIII), in which $R_B$ is —$OCH_3$, and $R_5$ and $R_7$ are as defined for the compounds of formula (I)

Methanol (50 ml) was added to the 3-aminobenzoic acid derivative of formula (XIV), in which $R_5$ and $R_7$ are as defined for the compounds of formula (I) to be preferred (0.1 mol). The mixture was cooled in an ice bath, slowly added with conc. $H_2SO_4$ (3 ml). The components were mixed and refluxed for 1 h. The solution was cooled, decanted in a separatory funnel containing 50 ml water, and taken up with t-butylmethylether (35 ml). Once mixing had been completed, the aqueous layer was drawn off and the ethereal phase was washed with water (25 ml) and then with 1.5M NaHCO$_3$ (25 ml). The ethereal phase was then evaporated under a suction tube.

b) Preparation of the derivative of formula (X), in which $R_C$ is —$OCH_3$ and $R_D$ is $CH_3$, $R_5$ and $R_7$ are as defined for derivative (I)

The derivative of formula (XIII) obtained in a) (0.1 mol) was added to acetic acid (5 ml).

The resulting mixture was heated slightly above 100° C., stirred, cooled to 100° C., added with acetic anhydride (1.3 ml), stirred until the temperature decreased to 75° C., and added with water (1 ml).

Water was removed under vacuum and the resulting oily syrup was resuspended in cyclohexane (5 ml). The temperature was raised while the syrup was freed from traces of water as cyclohexane-water azeotrope. Yields were about 89% to 95%.

Method C: Conversion of phthalic acid derivatives of formula (VII), in which $R_A$ is a protective group of the —OH function, into the corresponding derivatives of formula (II)A Step 1): Preparation of the derivative of formula (VIII) [$R_A$=protective group of the —OH function; $R_C$=—$CH_3$, and $R_2$, $R_3$, $R_4$ are as defined for the desired derivative of formula (I) to be prepared]

A solution of phthalic acid derivative of formula (VII), in which $R_A$ is a protective group of the —OH function, prepared as per Example A (0.1 mol) in 100 ml methanol, was added with CuCl (0.1 mol) and HCl (0.1 mol). The resulting mixture was heated to reflux for 30 min.

The clear solution obtained was evaporated to dryness under reduced pressure.

The resulting residue was dissolved in 1:3 water:methanol and acidified.

The title product was separated by cooling, collected by filtration, and air dried.

Yields were about 63% to 66%.

Step 2): Preparation of the derivative of formula (IX) [$R_A$=protective group of the —OH function; $R_C$=—$CH_3$, and $R_2$, $R_3$, $R_4$ are as defined for the derivatives of formula (I), and Hal=Cl]

The derivative of formula (VIII) obtained in step 1) (0.1 mol) was suspended in thionyl chloride (1.5 ml). The resulting suspension was slowly heated to the reflux temperature and maintained at said temperature until complete dissolution of the solid material.

After refluxing for further 30 min, excess thionyl chloride was removed under reduced pressure. The resulting residue was recrystallized from toluene.

Yields were about 80% to 90%.

Step 3): Preparation of diarylketone of formula (XI) [$R_A$=protective group of the —OH function; $R_B$=—$OCH_3$, $R_C$=$CH_3$, $R_D$=$CH_3$, and $R_2$, $R_3$, $R_4$ $R_5$ and $R_7$ are as defined for the compounds of formula (I)

0.1 mol of compound of formula (IX) obtained in Step 2) above and 0.1 mol of compound of formula (X) obtained as per Example B above were caused to react in a 10×100 mm test tube.

The reaction mixture was cooled in an ice bath and added with anhydrous $AlCl_3$ (200 mg). The tube was plugged with a baffle connected to a Teflon tube in a moistened cotton pad, used to entrap the HCl evolving during the reaction. The tube content was accurately mixed and cautiously heated in hot water. Gaseous HCl release was controlled by repeatedly heating and cooling the reaction mixture.

The reaction was continued for about 15 min and the temperature was raised to 50° C. until no further gas release was observed.

The reaction mixture was cooled in an ice bath and added with 1 g of ice in small pieces. Each piece of ice was allowed to react before addition of the next piece. The tube content was mixed accurately, cooled to room temperature, added with 0.5 ml water and 5 ml t-butylether. After mixing, the aqueous phase was drawn off. Extraction was repeated. Conc. HCl (0.2 ml) was added to 0.5 ml water. The organic layer was transferred into a small test tube and evaporated to dryness.

Yield was about 80%.

Step 4): Preparation of diarylketone of formula (II)A [in which $R_A$=protective group of the —OH function; $R_2$, $R_3$, $R_4$ $R_5$ and $R_7$ are as defined for the compounds of formula (I), to be prepared, corresponding to the diarylketone of formula (II), in which $R_A$=protective group of the —OH function, $R_B$=—OH and $R_C$=H, and $R_2$, $R_3$, $R_4$, $R_5$ and $R_7$ are as defined for the compounds of formula (I)]

The diarylketone of formula (XI) obtained in 3) above (0.1 mol) was treated with a 50:50 water/ethanol mixture (3 ml) containing about 1.89 to 3.6 g NaOH. The mixture was cautiously heated to reflux in a sand bath for 30 min. Once the reaction had been completed, the solution was acidified, the precipitate was collected by filtration and air dried. The yield in the final product was about 90%.

Method D: Preparation of compounds of formula (I)

Step a): Preparation of the compound of formula (III) [$R_A$=protective group of the —OH function; $R_B$=—OH, and $R_2$, $R_3$, $R_4$, $R_5$, and $R_7$ are as defined for the compounds of formula (I)]

0.01 mol of intermediate of formula (II), in which $R_A$ is a protective group of the —OH function; $R_B$=—OH, $R_C$ is H, and $R_2$, $R_3$, $R_4$, $R_5$, and $R_7$ are as defined for the compounds of formula (I), was suspensed in 30 ml of conc. strong acid, such as $H_2SO_4$ or $CF_3SO_3H$, preferably $CF_3SO_3H$. The resulting mixture was heated to 150° C. for 2 h under constant stirring. Two hours later, the solution was cooled to room temperature and neutralised with 10% aqueous NaOH.

The precipitate was filtered, washed with water and evaporated to dryness. A crystalline product was obtained corresponding to 0.0089 mol of the title intermediate of formula (III). Total yield: about 80% to 90%.

The product was analysed by TLC on silica gel and identified by IR spectrometry. The analytical values were in agreement with the theoretical values.

Steps b'and b"): Preparation of the compound of formula (IV) [$R_A$=protective group of the —OH function, and $R_2$, $R_3$, $R_4$, $R_5$ and $R_7$ are as defined for the desired compounds of formula (I) to be prepared]

The intermediate of formula (III) obtained in a) above (0.01 mol) was dissolved in a 1:3 v/v sulphuric acid/water mixture in a quantity about ranging from 20 to 35 ml. The resulting mixture was cooled to 0° C./5° C., stirred until complete dissolution of intermediate (III), added with 0.015 mol of $NaNO_2$, dissolved in 10 ml cold water (5° C.). The reaction mixture was stirred for additional 15 min and then added with 1:1 (v/v) sulphuric acid/water mixture (100 ml). The solution was heated to 150° C. for 1 h under constant stirring. After cooling to room temperature, the resulting precipitate was collected by filtration under vacuum, washed with water and dried under reduced pressure at 50° C. A yellow-brown crystalline solid was obtained, corresponding to about 0.0085 mol of the title intermediate of formula (IV).

Step c): Preparation of the compound of formula (V) [$R_2$, $R_3$, $R_4$, $R_5$ and $R_7$ are as defined for the compounds of formula (I)]

The intermediate of formula (IV) obtained in b) above was suspended in 100 ml glacial acetic acid containing 10 ml of a 48% HBr solution in water. The reaction mixture was heated to reflux for 3 h, cooled to room temperature, and filtered.

The precipitate obtained was collected by filtration under vacuum, washed with water, and dried under reduced pressure. Recrystallisation from methanol gave a yellow-greenish needle-shaped product. Yield was about 70% to 85%.

The analytical, IR and Rf values were in agreement with the values of the title products.

Step d): Preparation of the derivatives of formula (I) [$R_1$=$R_8$=—$OCOCH_3$, $R_6$,=—COOH, and $R_2$, $R_3$, $R_4$, $R_5$ and $R_7$ are as defined for the compounds of formula (I)] to be prepared The rhein derivative of formula (V) obtained in c) above (0.01 mol) was suspended in 100 ml glacial acetic acid, added with acetic anhydride (0.03 mol) and with one drop of conc. sulphuric acid, heated to 80° C. under stirring for 1 h. The solution was allowed to cool to room temperature. A yellow-greenish precipitate was collected by filtration under vacuum, washed with water and dried under reduced pressure. The total product yield was 90%–98%.

IR spectrum: $v_{max}$ 1733 $cm^{-1}$ (ester), 1701 $cm^{-1}$ (carboxyl), 1689 $cm^{-1}$ (carbonyl).

EXAMPLE 1

The compounds of formula (I), where $R_2=R_4=R_5=H$ and where $R_1$, $R_3$, $R_6$, $R_7$ and $R_8$ are as defined in Table 1, were prepared by general methods A, B, C, and D described above.

TABLE 1

| Compound | $R_1$ | $R_3$ | $R_6$ | $R_7$ | $R_8$ |
|---|---|---|---|---|---|
| D1 | —$OCH_3$ | —$OCH_3$ | —COOH | H | —$OCH_3$ |
| D2 | —OiPr | H | —COOEt | —$(CH_2)_2CH_3$ | —OH |
| D3 | —OAc | H | —$CONHR_2$ | $C_3$—$C_5$alkyl | —OH |
| D4 | —OH | H | —COOMe | —$CH_2CH=CH_2$ | —OH |
| D5 | —OH | H | —COOH | —$CH_2Ph$ | —OH |
| D6 | —OAc | H | —$CH_2OAc$ | —$CH_3$ | —OAc |
| D7 | —OMe | H | —COOH | $CH_2Ph$ | —OH |

Me=methyl; Ac=—$OCOCH_3$; $R_2=C_1-C_4$ alkyl; iPr=isopropyl; Et=ethyl; Ph=$C_6H_5$ phenyl.

In particular, the starting raw materials used were the diphenylketones of formula (II), in which $R_B$=OH, $R_C$=H, $R_2=R_4=R_5$=H, $R_3$ and $R_7$ are as defined in Table 1 for the desired compounds of formula (I), and —$OR_A$ corresponds to $R_1$ as defined in Table 1 for compounds D1, D2, D3, D6 and D7; or —$OR_A$ is —$OCH_3$ for compounds D4, D5 and D6. Steps a), b'), b"), and optionally c), were carried out as per Method D, to convert said materials into the corresponding derivatives of formulas (II), (IV) and (V).

Acetylation, reduction of —COOH, esterification of —COOH, or conversion of —COOH into amide were carried out when required to obtain the compounds of formula (I) listed in Table 1.

The preparation of the single compounds is described hereinafter in more detail.

EXAMPLE 1a

Preparation of compounds D1, D4, D5, D6, and D7

The derivatives of formula (II)A, in which $R_A$=—$CH_3$, $R_2=R_4=R_5$=H, and $R_3$ and $R_7$ are as defined in Table 1 for the desired compounds of formula (I), corresponding to the derivatives of formula (II), in which $R_C$=H, $R_B$ is —OH, $R_A$ is —$CH_3$, $R_2=R_4=R_5$=H, $R_3$ and $R_7$ are as defined in Table 1, were prepared as per Methods A), B) and C). In particular, the procedures were as follows:

Method A the compounds of formula (VII), in which $R_A$=$CH_3$, and $R_2=R_4$=H, $R_3$ and $R_7$ are as defined in Table 1 for the corresponding compounds of formula (I), were prepared.

Method C, step 1 the resulting compounds of formula (VII) were converted into is the corresponding compounds of formula (VIII), in which $R_C$=$CH_3$ [$R_A$=$CH_3$, $R_2=R_4$=H, $R_3$ and $R_7$ are as defined in Table 1 ];

Method C, step 2 the resulting compounds of formula (VIII) were converted into the corresponding compounds of formula (IX), in which Hal=Cl [$R_A$=$CH_3$, $R_C$=$CH_3$, $R_2=R_4$=H, $R_3$ and $R_7$ are as defined in Table 1];

Method C, step 3 the resulting compounds of formula (IX) were reacted with the derivatives of formula (X), in which $R_D$=$CH_3$, $R_B$=$CH_3$, $R_5$=H and $R_7$ is as defined in Table 1 for the corresponding desired derivative of formula (I), obtained as per Example B, to give the corresponding compounds of formula (XI), in which $R_A=R_C=R_D$=$CH_3$, $R_B$=$OCH_3$, $R_2=R_4=R_5$=H, and $R_3$ and $R_7$ are as defined in Table 1;

Method C, step 4 the resulting compounds of formula (XI) were converted into the corresponding derivatives of formula (II)A, in which $R_A$=$CH_3$, [$R_2=R_4=R_5$=H, $R_3$ and $R_7$ are as defined in Table 1] corresponding to the compounds of formula (II), in which $R_A$=$CH_3$, $R_C$=H, $R_B$OH [$R_2=R_4=R_5$=H, $R_3$ and $R_7$ are as defined in Table 1].

Method D, step a)

the resulting compounds of formula (II) gave the corresponding compounds of formula (III) [$R_A$=$CH_3$, $R_{B-OH}$, $R_2=R_4=R_5$=H, $R_3$ and $R_7$ are as defined in Table 1];

Method D, steps b') and b")

the resulting compounds of formula (III) gave the corresponding compounds of formula (IV) [$R_A$=$CH_3$, $R_2=R_4=R_5$=H, $R_3$ and $R_7$ are as defined in Table 1];

Method D, step c)

the resulting compounds of formula (IV) gave the corresponding compounds of formula (V) [$R_2=R_4=R_5$=H, $R_3$ and $R_7$ are as defined in Table 1];

Compound D1 the corresponding compound of formula (IV) obtained in step b") above, in which $R_A$ is $CH_3$ (and, therefore, —$OR_A$ corresponds to $R_1$ as defined in Table 1 for D1) was converted into D1by etherification according to techniques conventionally adopted in the field of anthraquinone derivatives, e.g. by treatment with a base, such as NaH, and with a methylating agent, such as $CH_3I$.

Compound D4 the corresponding compound of formula (V) obtained in step c) above [in which $R_2=R_4=R_5$=H, $R_3$=H, $R_7$=—$CH_2CH=CH_2$] was converted to D4 by esterification according to conventional techniques, e.g. by treatment with methanol, in the presence of an acid as catalyst.

Compound D5 compound D5 corresponds to compound (V) obtained in step c) above, when compound (V), in which $R_2=R_4=R_5$=H, $R_3$=H, $R_7$=—$CH_2Ph$, where Ph is a phenyl, was used.

Compound D6 the corresponding compound of formula (V) obtained in step c) above [in which $R_2=R_4=R_5$=H, $R_3$=H, $R_7$=—$CH_3$] was converted into compound D6 by reduction with $LiBH_4$, followed by treatment of the resulting compound with acetic anhydride, in the presence of a strong acid as catalyst, such as conc. sulphuric acid, e.g. under the operating conditions as per step d).

Compound D7 the corresponding derivative of formula (IV) obtained in step b") above [in which $R_2=R_4=R_5$=H, $R_3$=H, $R_7$=—

$CH_2Ph$, where Ph is a phenyl, —$OR_A$=$R_1$=—$OCH_3$], corresponds to compound D7 itself.

EXAMPLE 1b

Preparation of compounds D2 and D3 Compound D2
Method A the compound of formula (XII), in which $R_A$ is iPr (isopropyl), $R_2$=$R_4$=H, $R_3$=H as defined in Table 1 for compound D2, was converted into the corresponding compound of formula (VII), in which $R_A$ is iPr (isopropyl), $R_2$=$R_4$=$R_3$=H;

Method C, steps 1) and 2)

the resulting compound of formula (VII), was converted into the compound of formula (VIII), in which $R_A$ is iPr (isopropyl), $R_2$=$R_4$=$R_3$=H, $R_C$=$CH_3$, and, respectively, into the compound of formula (IX), in which $R_A$ is iPr (isopropyl), $R_2$=$R_4$=$R_3$=H, $R_c$=$CH_3$, and Hal=Cl;

Method C, step 3)

the resulting compound of formula (IX) was reacted with the compound of formula (X), in which $R_D$ is —$CH_3$, $R_B$ is —$OCH_3$, $R_5$=H and $R_7$ is —$(CH_2)_2CH_3$, as defined in Table 1 for D2, obtained as per Example B, to give the derivative of formula (XI) in which $R_A$ is iPr (isopropyl), $R_2$=$R_4$=$R_3$=$R_5$=H, $R_C$=$R_D$=—$CH_3$, $R_7$=—$(CH_2)_2CH_3$;

Method C, step 4)

the resulting compound of formula (XI) was converted into the derivative of formula (II)A, in which $R_A$ is iPr (isopropyl), $R_2$=$R_4$=$R_3$=$R_5$=H, $R_7$=—$(CH_2)_2CH_3$ corresponding to derivative (II), in which $R_C$ is H, $R_B$ is OH, $R_A$ is iPr (isopropyl), $R_2$=$R_4$=$R_3$=$R_5$=H, $R_7$=—$(CH_2)_2CH_3$;

Method D, steps a), b') and b")

the resulting compound of formula (II) was converted into the compounds of formula (III), in which $R_B$ is OH, $R_A$ is iPr (isopropyl), $R_2$=$R_4$=$R_3$=$R_5$=H, $R_7$=—$(CH_2)_2CH_3$, and, respectively, into the compound of formula (IV), in which $R_A$ is iPr (isopropyl), $R_2$=$R_4$=$R_3$=$R_5$=H, $R_7$=—$(CH_2)_2CH_3$.

Esterification of compound (IV)

the resulting compound of formula (IV) was converted into compound D2 of formula (I), in which $R_1$ is —OiPr, $R_8$ is —OH, $R_2$=$R_4$=$R_3$=$R_5$=H, $R_7$=—$(CH_2)_2CH_3$, $R_6$=—COOEt, by conventional methods, e.g. by treatment with EtOH, in the presence of conc. $H_2SO_4$.

Compound D3
Method C, steps 1 through 4)

using the compounds of formula (VII), in which $R_A$ is $CH_3$, $R_2$=$R_4$=$R_3$=H (obtained as per Example A) and the compounds of formula (X), in which $R_D$ is $CH_3$, $R_B$ is $OCH_3$, $R_5$=H, and $R_7$ is a $C_3$-$C_5$ alkyl group (obtained as per Example B), the diphenylketone of formula (II)A, in which $R_A$ is $CH_3$, $R_2$=$R_4$=$R_5$=H, $R_3$=H and $R_7$ is a $C_3$-$C_5$ alkyl group as defined in Table 1 for D3, corresponding to the compounds of formula (II), in which $R_A$ is $CH_3$, $R_C$=H, $R_B$=OH, $R_2$=$R_4$=$R_5$=H, and $R_3$=H and $R_7$ is a $C_3$-$C_5$ alkyl group.

Demethylation and acetylation the resulting diphenylketone of formula (II) was treated with HBr in glacial acetic acid (under operating conditions analogous to those described for Method D), step c) and then converted by conventional methods into the corresponding compound of formula (II), in which $R_A$ is —$COCH_3$, e.g. by treatment with acetic anhydride under operating conditions analogous to those described for Method D, step d).

Method D, steps a), b') and b")

the resulting diphenylketone of formula (II), in which $R_A$ is —$COCH_3$, $R_C$=H, $R_B$=OH, $R_2$=$R_4$=$R_5$=H, $R_3$=H and $R7$=$C_3$-$C_5$ alkyl, was converted into the corresponding compounds of formula (III), in which $R_A$ is —$COCH_3$, $R_B$=OH, $R_2$=$R_4$=$R_5$=H, $R_3$=H and $R_7$=$C_3$-$C_5$ alkyl; and of formula (IV) in which $R_A$ is —$COCH_3$, $R_B$=OH, $R_2$=$R_4$=$R_5$=H, $R_3$=H and $R_7$=$C_3$-$C_5$ alkyl;

Preparation of amides the resulting compounds of formula (IV) were converted into the corresponding compounds D3, by treatment with the corresponding amines $R_2NH$, where R are $C_1$-$C_4$ alkyl groups, by conventional methods, or else were first converted into esters by reaction with an alcohol and then into amides by reaction with the aforesaid amines.

EXAMPLE 2

Acetylation of 1,8-dihydrooxyanthraquinone 1,8-dihydroxyantraquinone (10 g; M.W. 268; 0.037 moles) is suspended in acetic anhydride (153 ml; 151.9 g; 1.48 moles) and the mixture stirred for 10 minutes. Sodium acetate (3 g) and activated charcoal (1 g) are added and the suspension heated to 90° C./95° C. for about 30 minutes–1 hour.

The activated charcoal is filtered off from the solution and the filtrate at 90° C. is mixed with 1.7 ml of sulphuric acid (95%). Subsequently, while stirring the solution is cooled quickly to room temperature (e.g. 20° C.) and the resulting suspension is filtered. The residue is washed free of sulfate with demineralized water. 1,8-diacetylantraquinone was obtained in 88% yield. Melting point was 228°–330° C. and elemental analysis was in agreement with theoretical data.

EXAMPLE 3

Mononitration of 1,8-diacetylanthraquinone

A solution of nitric acid (fuming $HNO_3$ 100%; 0.1 ml; d=1.52; 152 mg: M.W. 63; 2.4 mmoles) and concentrated sulfuric acid (2.9 ml) (volume ratio 1:30) was mixed with 1,8-diacetylantraquinone (1 g; M.W. 352; 2.84 mmoles). The mixture was maintained at 5° C. for 30 minutes under constant stirring. At the end of this time period the mixture was filtered, washed with water and dried at 50° C. Yield of mono-nitro 1,8-diacetylantraquinone was 67%.

EXAMPLE 4

Preparation of 3-carboxy-1,8-diacetylanthraquinone by means of cyanide treatment of mono-nitro 1,8-diacetylanthraquinone Mono-nitro 1,8-diacetylantraquinone (1 g; M.W. 397; 2.52 mmoles) was added to 10 ml of a mixture tetrahydrofuran: water=20:80 by volume. The mixture was heated to 50° C. under constant stirring followed by addition of NaCN (1.4 g; M.W. 49; 28.57 moles). The reaction mixture was maintained overnight at 50° C. under constant agitation. The resulting mixture was filtered and washed with water. The bright yellow-greenish crystals were dried at 50° C. 3-carboxy-1,8-diacetylantraquinone was obtained in a 44% yield.

I claim:

1. A process for the preparation of a rhein derivative of formula (XV)

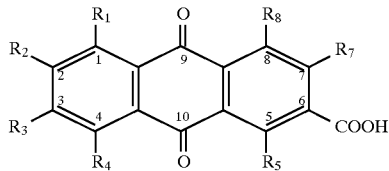

(XV)

wherein $R_1$ is selected among —ORa and —OCORa, and $R_8$ is selected among —ORb and —OCORb, wherein Ra and Rb, equal or different one from another, are selected from the group consisting of H, alkyl group and aromatic group;

$R_2$, $R_3$, $R_4$, $R_5$, and $R_7$, equal or different one from another, are selected among H, alkyl, alkenyl, alkinyl, hydroxy, alkoxy, acyloxy, arylalkyl, aromatic and cyano group, provided that at least one of $R_5$ and $R_7$ is H, comprising the following steps:

e) subjecting to mono-nitration an anthraquinone derivative of formula (XVI)

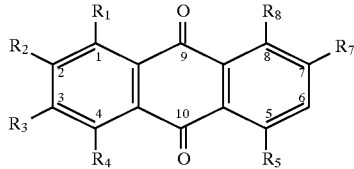

(XVI)

wherein $R_1$, $R_8$, $R_2$, $R_3$, $R_4$, $R_5$ and $R_7$, are as above defined for compound of formula (XV), by treating the compound of formula (XVI) with an essentially stoichiometric amount of nitric acid, thus affording the corresponding mono-nitro derivative selected from the group consisting of compound of formula (XVII)A, compound of formula (XVII)B and mixtures thereof,

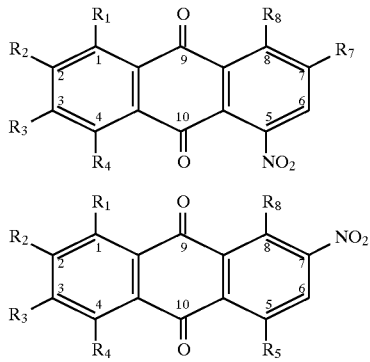

(XVII)A (XVII)B wherein $R_1$, $R_8$, $R_2$, $R_3$, $R_4$, $R_5$ and $R_7$, are as above defined for compound of formula (XVI);

f) treating the mono-nitro derivative obtained from the preceding step with cyanide ions, to give the carboxy anthraquinone derivative of formula (XV) as above defined.

2. The process according to claim 1, wherein step e) is carried out on anthraquinone derivative of formula (XVI) wherein $R_1$ and $R_8$ are as above defined in step e), and $R_2=R_3=R_4=R_5=R_7=H$, hereinbelow represented as compound of formula (XVI)A,

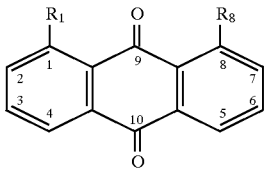

(XVI)A wherein $R_1$ and $R_8$ are as above defined in step e), affording the corresponding compound of formula (XVII)A and (XVII)B, wherein $R_1$ and $R_8$ are as above defined in step e) and $R_2$, $R_3$, $R_4$, $R_5$ and $R_7$ are H, hereinbelow represented with formula (XVII)C and (XVII)D

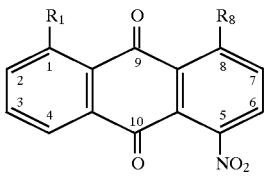

(XVII)C (XVII)D wherein $R_1$ and $R_8$ are as above defined in step e), which are then converted by means of step f) into the corresponding carboxylic acid of formula (XV) wherein $R_1$ and $R_8$ are as above defined in step e), and $R_2=R_3=R_4=R_5=R_7$H, hereinbelow represented with formula (XV)A

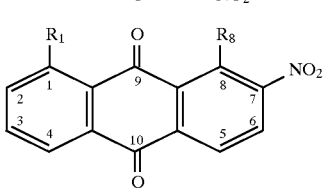

(XV)A wherein $R_1$ and $R_8$ are as above defined in step e).

3. The process according to claim 1, wherein mono-nitration according to step e) is carried out on substrate of formula (XVI) or (XVI)A wherein $R_1$ and $R_8$ are —O—acyl groups —OCORa and —OCORb, wherein Ra and Rb are as above defined for step e), affording by means of step e) the corresponding derivatives of formula (XVII)A, (XVII)B or mixtures thereof, or (XVII)C, (XVII)D or mixtures thereof, and then by means of step f) the corresponding derivatives of formula (XV) or (XV)A, wherein $R_1$ and $R_8$ have the same meaning.

4. The process according to claim 2, wherein $R_1$ and $R_8$ are —OCORa and —OCORb respectively, wherein Ra and Rb, equal or different one from another, are C1–C4 alkyl groups.

5. The process according to claim 4, wherein Ra=Rb=—CH3 groups, and the process produces diacer- hein [compound of formula (XV)A wherein $R_1=R_8=$— OCOCH$_3$].

6. The process according to claim 5, further comprising preparing compounds of formula (XVI) or (XVI)A wherein $R_1=R_8=$—OCOCH$_3$ by treating the corresponding 1,8 dihydroxyanthraquinones with acetic anhydride, used in excess, as the reaction medium, in the presence of sodium acetate as the catalyst, at temperatures of from 80° C. to 100° C.

7. The process according to claim 1 wherein nitric acid is used in an amount ranging from 0.8:1 to about 1.2:1 moles per mole of compound of formula (XVI) or (XVI)A.

8. The process according to claim 1, wherein in step e) nitric acid is used in an amount ranging from 0.8:1 to 1.0:1.

9. The process according to claim 1, wherein step e) is carried out in diluted solution of nitric acid in sulphuric acid, with nitric acid:sulphuric acid ratios comprised from 1:1000 to 1:30 volume/volume (v/v), referred to pure $HNO_3$ acid and concentrated $H_2SO_4$, wherein concentrated sulphuric acid is at least 90% w/w (weight/weight) $H_2SO_4$ in water.

10. The process according to claim 1, wherein step e) is carried at a temperature comprised between $-50°$ C. to $+5°$ C.

11. The process according to claim 1, wherein step e) is carried at a temperature of $-40°$ C.

12. The process according to claim 1, wherein in step f), the cyanide ions source is an alkaline or alkaline-earth cyanide; the reaction temperature is comprised between $+20°$ C. and $+100°$ C.; the cyanide ions are added in a stoichiometric excess with respect to the substrate; and the reaction is carried out in water optionally admixed with a co-solvent.

13. The process according to claim 1, wherein in step f) the reaction temperature is comprised between $+40°$ C. and $60°$ C.

14. The process according to claim 1, wherein in step f) cyanide: substrate molar ratios are comprised between 20:1 and 5:1.

15. The process according to claim 1, wherein step f) is carried out in tetrahydrofuran: water mixtures in ratios about of from 50:50 to 10:90.

16. The process according to claim 1, wherein rhein derivatives of formula (I)

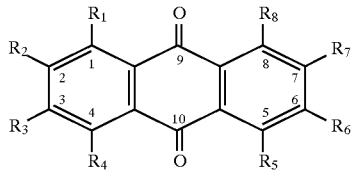

wherein $R_2=R_4=R_5=H$ and where:

$R_1$ is —ORa or —OCORa, and $R_8$ is ORb or —OCORb, where Ra and Rb, which may be the same or different one from another, each present H, alkyl or aromatic group, $R_6$ is —COORc, —CONRdRe, —CH2OCORf, —CH2ORg, where Rc, Rd, Re and Rf, which may be the same or different one from another, each represents H, alkyl or aromatic group, and Rg is an alkyl or aromatic group, $R_3$ is H, —ORh or —OCORh where Rh is H, alkyl or aromatic group;

$R_7$ is H, alkyl, alkenyl, alkynyl or arylalkyl group, and pharmaceutically acceptable salts thereof, provided that at least $R_3$ or $R_7$ is different from H, and being further provided that the compounds of formula (I), where $R_2=R_4=R_5=$ H selected among those where:

$R_6$ is —COOH or —$CH_2OH$, and $R_1=R_8=R_3=$—OH;

$R_6$ is —$COOCH_2CH_3$ or —$CH_2OCOCH_3$; $R_1=R_3=$—$OCH_3$ and $R_8=$—OH, and $R_6$ is —COOH, —$COOCH_2CH_3$ or —$CH_2OCOCH_3$, $R_3=$—$OCH_3$ and $R_1=R_8=$—OH, are excluded, are obtained by mono-nitrating according to step e) derivatives of formula (XVI) wherein $R_1$, $R_2$, $R_3$, $R_4$, $R_5$, $R_7$ and $R_8$ are as defined for the aforementioned rhein derivatives of formula (I), provided that at least one of $R_5$ and $R_7$ is H, then subjecting the corresponding mono-nitro derivatives of formula (XVII)A, (XVII)B or mixtures thereof, or (XVII)C, (XVII)D or mixture thereof thus obtained to rearrangement by treatment with cyanide ions according to step f).

17. The process according to claim 1, wherein step e) is carried out on anthraquinone derivative of formula (XVI) wherein $R_1=R_8=$—$OCOCH_3$ and $R_2=R_3=R_4=R_5=R_7=H$, hereinbelow represented as compound of formula (XVI)A,

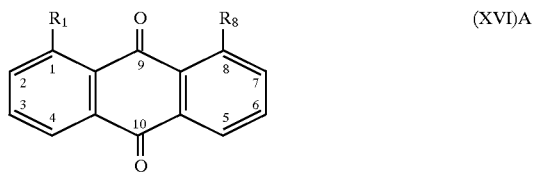

wherein $R_1=R_8=$—$OCOCH_3$, affording the corresponding compound of formula (XVII)A and (XVII)B, wherein $R_1=R_8=$—$OCOCH_3$, and $R_2$, $R_3$, $R_4$, $R_5$ and $R_7$ are H, hereinbelow represented with formula (XVII)C and (XVII)D

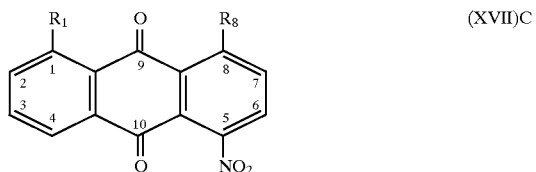

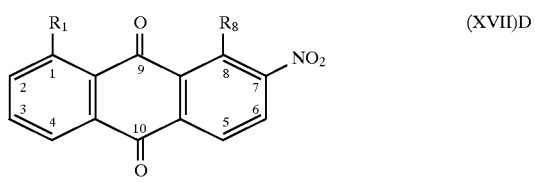

wherein $R_1=R_8=$—$OCOCH_3$, which are then converted by means of step f) into the corresponding carboxylic as of formula (XV) and $R_2=R_3=R_4=R_5=R_7=H$, hereinbelow represented with formula (XV)A

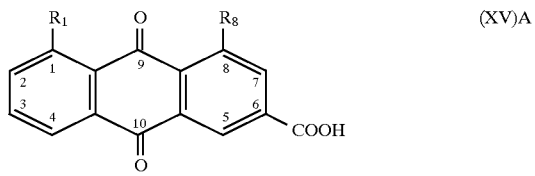

wherein $R_1=R_8=$—$OCOCH_3$.

* * * * *